US011291355B2

(12) United States Patent
Lund et al.

(10) Patent No.: US 11,291,355 B2
(45) Date of Patent: Apr. 5, 2022

(54) METHOD FOR FIXATION OF A WIRE PORTION OF AN ENDOSCOPE, AND AN ENDOSCOPE

(71) Applicant: AMBU A/S, Ballerup (DK)

(72) Inventors: Jesper Grøndahl Lund, Ballerup (DK); Michael Kappler Hansen, Vallensbæk (DK)

(73) Assignee: AMBU A/S, Ballerup (DK)

(*) Notice: Subject to any disclaimer, the term of this patent is extended or adjusted under 35 U.S.C. 154(b) by 463 days.

(21) Appl. No.: 16/250,985

(22) Filed: Jan. 17, 2019

(65) Prior Publication Data

US 2019/0216298 A1 Jul. 18, 2019
US 2020/0121169 A9 Apr. 23, 2020

(30) Foreign Application Priority Data

Jan. 19, 2018 (EP) .................................... 18152532
Aug. 16, 2018 (DK) ........................... PA 2018 70530

(51) Int. Cl.
*A61B 1/005* (2006.01)
*A61B 1/00* (2006.01)
*A61B 1/018* (2006.01)

(52) U.S. Cl.
CPC .......... *A61B 1/0057* (2013.01); *A61B 1/0011* (2013.01); *A61B 1/0052* (2013.01);
(Continued)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/008; A61B 2017/003; A61B 2017/00318; A61B 2017/00323; A61B 2017/00327;
(Continued)

(56) References Cited

U.S. PATENT DOCUMENTS

| 609,570 A | 8/1898 | Bowden |
| 609,750 A | 8/1898 | Bowden |

(Continued)

FOREIGN PATENT DOCUMENTS

| AU | 2008/207558 | 4/2009 |
| CN | 1692872 | 11/2005 |

(Continued)

OTHER PUBLICATIONS

Extended European Search Report issued by the European Patent Office, dated Jul. 11, 2018, in related European Patent Application No. 18152532.0-1124; 7 pages.

*Primary Examiner* — Ryan N Henderson
(74) *Attorney, Agent, or Firm* — Faegre Drinker Biddle & Reath LLP

(57) ABSTRACT

An endoscope made by a method for fixation of portions of steering wire of the endoscope, the steering wire having a first portion, a second portion, and a third portion, the method including positioning the second wire portion and the third wire portion of the steering wire adjacent to each other, applying an adhesive, at least partly enclosing the second wire portion, the third wire portion, and the adhesive with a crimp shell, and crimping the crimp shell, the second wire portion, and the third wire portion to thereby fixate the second wire portion in relation to the third wire portion.

18 Claims, 8 Drawing Sheets

(52) U.S. Cl.
CPC ...... *A61B 1/00066* (2013.01); *A61B 1/00087* (2013.01); *A61B 1/00098* (2013.01); *A61B 1/00101* (2013.01); *A61B 1/018* (2013.01)

(58) Field of Classification Search
CPC .......... A61M 25/0133; A61M 25/0136; A61M 25/0147; A61M 2025/015
See application file for complete search history.

(56) References Cited

U.S. PATENT DOCUMENTS

| | | | |
|---|---|---|---|
| 2,849,548 A | 8/1958 | Young | |
| 3,958,566 A | 5/1976 | Furihata | |
| 4,203,430 A | 5/1980 | Takahashi | |
| 4,745,908 A | 5/1988 | Wardle | |
| 4,750,475 A | 6/1988 | Yoshihashi | |
| 4,757,827 A | 7/1988 | Buchbinder | |
| 4,805,596 A | 2/1989 | Hatori | |
| 4,832,473 A | 5/1989 | Ueda | |
| 4,926,172 A | 5/1990 | Gorsek | |
| 5,122,125 A | 6/1992 | Deuss | |
| 5,167,221 A | 12/1992 | Chikama | |
| 5,170,775 A | 12/1992 | Tagami | |
| 5,179,934 A | 1/1993 | Nagayoshi et al. | |
| 5,275,151 A | 1/1994 | Shockey | |
| 5,299,562 A | 4/1994 | Heckele | |
| 5,327,881 A | 7/1994 | Greene | |
| 5,347,989 A | 9/1994 | Monroe et al. | |
| 5,429,620 A | 7/1995 | Davis | |
| 5,455,880 A * | 10/1995 | Reid ................... | G02B 6/3834 385/87 |
| 5,462,527 A | 10/1995 | Stevens-Wright et al. | |
| 5,480,203 A * | 1/1996 | Favalora ................. | B25B 25/00 24/115 N |
| 5,512,035 A | 4/1996 | Konstorum et al. | |
| 5,541,622 A | 7/1996 | Engle et al. | |
| 5,544,902 A | 8/1996 | Belter | |
| 5,607,386 A | 3/1997 | Flam | |
| 5,626,553 A | 5/1997 | Frassica et al. | |
| 5,643,174 A | 7/1997 | Yamamoto et al. | |
| 5,752,912 A * | 5/1998 | Takahashi ............ | A61B 1/0052 600/146 |
| 5,785,663 A | 7/1998 | Sarvazyan | |
| 5,810,876 A | 9/1998 | Kelleher | |
| 5,879,289 A | 3/1999 | Yarush | |
| 5,888,192 A | 3/1999 | Heimberger | |
| 5,889,507 A | 3/1999 | Engle et al. | |
| 5,913,816 A | 6/1999 | Sanders et al. | |
| 5,938,588 A | 8/1999 | Grabover | |
| 6,007,531 A | 12/1999 | Snoke | |
| 6,117,071 A | 9/2000 | Ito et al. | |
| 6,200,294 B1 | 3/2001 | Liu | |
| 6,236,034 B1 | 5/2001 | DeVolpi | |
| 6,258,101 B1 | 7/2001 | Blake, III | |
| 6,270,508 B1 | 8/2001 | Klieman | |
| 6,440,062 B1 | 8/2002 | Ouchi | |
| 6,569,086 B2 | 5/2003 | Motoki et al. | |
| 6,684,562 B1 * | 2/2004 | Schade ................ | A01K 15/003 119/803 |
| 6,821,157 B2 | 11/2004 | Brändström et al. | |
| 6,829,497 B2 | 12/2004 | Mogul | |
| 7,300,438 B2 | 11/2007 | Falwell et al. | |
| 7,524,301 B2 | 4/2009 | Dubois et al. | |
| 7,591,784 B2 | 9/2009 | Butler | |
| 7,662,092 B2 | 2/2010 | Miyagi et al. | |
| 7,794,392 B2 | 9/2010 | Maruyama | |
| 7,828,725 B2 | 11/2010 | Maruyama | |
| 7,934,505 B2 | 5/2011 | Garren et al. | |
| 8,449,530 B2 | 5/2013 | Bacher et al. | |
| 8,790,250 B2 | 4/2014 | Petersen | |
| 8,821,389 B2 | 9/2014 | Yamane | |
| 9,125,582 B2 | 9/2015 | Petersen | |
| 9,162,036 B2 | 10/2015 | Caples et al. | |
| 9,678,275 B1 * | 6/2017 | Griffin .................. | G02B 6/262 |
| 10,149,605 B2 | 12/2018 | Petersen et al. | |
| 2001/0023313 A1 | 9/2001 | Ide | |
| 2001/0025135 A1 | 9/2001 | Naito et al. | |
| 2001/0041891 A1 * | 11/2001 | Thompson ........ | A61M 25/0147 606/41 |
| 2002/0099266 A1 | 7/2002 | Ogura | |
| 2002/0164130 A1 * | 11/2002 | Elkins, II ............ | G02B 6/3887 385/87 |
| 2003/0009176 A1 | 1/2003 | Bilitz | |
| 2003/0092965 A1 | 5/2003 | Konomura et al. | |
| 2004/0019256 A1 | 1/2004 | Cubb et al. | |
| 2004/0199052 A1 * | 10/2004 | Banik ................. | A61B 1/0051 600/142 |
| 2004/0220449 A1 | 11/2004 | Zirps et al. | |
| 2004/0267093 A1 | 12/2004 | Miyagi et al. | |
| 2005/0070764 A1 | 3/2005 | Nobis | |
| 2005/0075539 A1 | 4/2005 | Schulz | |
| 2005/0107667 A1 * | 5/2005 | Danitz ............. | A61B 17/07207 600/139 |
| 2005/0131279 A1 | 6/2005 | Boulais et al. | |
| 2005/0197536 A1 | 9/2005 | Banik et al. | |
| 2006/0025651 A1 | 2/2006 | Adler | |
| 2006/0111209 A1 * | 5/2006 | Hinman ................. | A61B 17/32 474/206 |
| 2006/0200047 A1 * | 9/2006 | Galdonik .......... | A61M 25/0138 600/585 |
| 2006/0258955 A1 | 11/2006 | Hoffman | |
| 2007/0219411 A1 | 9/2007 | Dejima | |
| 2007/0232858 A1 | 10/2007 | Macnamara et al. | |
| 2007/0255104 A1 | 11/2007 | Maruyama | |
| 2007/0282167 A1 | 12/2007 | Barenboym et al. | |
| 2007/0299311 A1 | 12/2007 | Sato et al. | |
| 2008/0051631 A1 | 2/2008 | Dejima et al. | |
| 2008/0051694 A1 | 2/2008 | Kato | |
| 2008/0188868 A1 | 8/2008 | Weitzner et al. | |
| 2008/0195128 A1 | 8/2008 | Orbay | |
| 2008/0249362 A1 | 10/2008 | Jiang et al. | |
| 2008/0287735 A1 | 11/2008 | Takemoto | |
| 2009/0054733 A1 | 2/2009 | Marescaux | |
| 2009/0076328 A1 | 3/2009 | Root | |
| 2009/0143647 A1 | 6/2009 | Banju | |
| 2009/0247994 A1 | 10/2009 | Bacher et al. | |
| 2010/0022837 A1 | 1/2010 | Ishiguro | |
| 2010/0030020 A1 | 2/2010 | Sanders | |
| 2010/0063512 A1 | 3/2010 | Braga et al. | |
| 2010/0069834 A1 * | 3/2010 | Schultz ............. | A61M 25/0147 604/95.04 |
| 2010/0106103 A1 | 4/2010 | Ziebol et al. | |
| 2010/0121147 A1 | 5/2010 | Oskin et al. | |
| 2010/0249497 A1 | 9/2010 | Peine | |
| 2010/0249639 A1 | 9/2010 | Bhatt | |
| 2010/0268268 A1 | 10/2010 | Bacher | |
| 2010/0298642 A1 | 11/2010 | Trusty | |
| 2011/0009694 A1 | 1/2011 | Schultz | |
| 2011/0054287 A1 * | 3/2011 | Schultz ............. | A61M 25/0136 600/374 |
| 2011/0152613 A1 * | 6/2011 | Zubiate ................ | A61B 1/0055 600/109 |
| 2011/0264129 A1 | 10/2011 | Holdgate | |
| 2011/0306831 A1 | 12/2011 | Køhnke et al. | |
| 2012/0220828 A1 | 8/2012 | Iwasaki et al. | |
| 2013/0074303 A1 * | 3/2013 | Durrant ................ | G02B 6/2558 29/402.14 |
| 2013/0137924 A1 | 5/2013 | Iwasaki et al. | |
| 2013/0204082 A1 | 8/2013 | Fischer, Jr. | |
| 2013/0281782 A1 | 10/2013 | Zhou | |
| 2014/0046123 A1 | 2/2014 | Connors et al. | |
| 2014/0073855 A1 | 3/2014 | Kindler | |
| 2014/0142377 A1 | 5/2014 | Yang | |
| 2014/0148759 A1 | 5/2014 | Macnamara et al. | |
| 2014/0206936 A1 | 7/2014 | Cooper et al. | |
| 2014/0243615 A1 | 8/2014 | Schaeffer et al. | |
| 2014/0257240 A1 * | 9/2014 | Burdulis ............ | A61B 17/3401 604/506 |
| 2014/0257249 A1 | 9/2014 | Witt | |
| 2014/0275763 A1 | 9/2014 | King et al. | |
| 2014/0336532 A1 | 11/2014 | Seguy | |
| 2014/0336573 A1 * | 11/2014 | Yu .................... | A61M 25/0136 604/95.04 |

(56) References Cited

U.S. PATENT DOCUMENTS

| | | |
|---|---|---|
| 2015/0216644 A1 | 8/2015 | Cahill et al. |
| 2015/0217092 A1 | 8/2015 | Kokate et al. |
| 2015/0335227 A1 | 11/2015 | Jacobsen et al. |
| 2015/0366435 A1* | 12/2015 | Williams .............. A61B 1/0052 600/149 |
| 2016/0100771 A1* | 4/2016 | Chiba ................... A61B 5/062 600/424 |
| 2016/0213232 A1* | 7/2016 | Katayama .............. A61B 1/041 |
| 2017/0108356 A1* | 4/2017 | Iida ....................... A61B 5/062 |
| 2017/0119481 A1 | 5/2017 | Romo et al. |
| 2017/0281296 A1 | 10/2017 | Cooper et al. |
| 2018/0028786 A1* | 2/2018 | Jungles ................ A61B 1/0052 |
| 2018/0042519 A1* | 2/2018 | Chiba .................... G01B 7/30 |
| 2018/0296068 A1 | 10/2018 | Matthison-Hansen et al. |
| 2018/0296069 A1 | 10/2018 | Matthison-Hansen et al. |
| 2018/0303315 A1 | 10/2018 | Matthison-Hansen et al. |
| 2018/0303316 A1 | 10/2018 | Matthison-Hansen et al. |
| 2018/0303317 A1 | 10/2018 | Matthison-Hansen et al. |
| 2018/0303472 A1 | 10/2018 | Matthison-Hansen et al. |
| 2018/0309908 A1* | 10/2018 | Matthison-Hansen ...................... A61B 1/0011 |
| 2019/0036234 A1* | 1/2019 | Stoltenberg ............. C09J 11/04 |
| 2019/0111236 A1* | 4/2019 | Oliverius ........... A61M 25/0147 |
| 2020/0014130 A1* | 1/2020 | Sato ......................... H01R 4/62 |
| 2020/0222667 A1* | 7/2020 | Tang .................. A61M 25/0113 |
| 2020/0312546 A1* | 10/2020 | Matsumoto ........... H01F 27/361 |

FOREIGN PATENT DOCUMENTS

| | | | |
|---|---|---|---|
| CN | 102271571 | 12/2011 | |
| EP | 0357274 | 3/1990 | |
| EP | 0567146 | 10/1993 | |
| EP | 1046406 | 10/2000 | |
| EP | 1484003 | 8/2004 | |
| EP | 1561413 | 8/2005 | |
| EP | 2067433 | 6/2009 | |
| EP | 2106751 | 7/2009 | |
| EP | 2288284 A2 | 3/2011 | |
| JP | S4991184 | 11/1947 | |
| JP | H0666619 | 3/1994 | |
| JP | H0910166 | 1/1997 | |
| JP | H11216103 | 8/1999 | |
| JP | 2003052618 | 2/2003 | |
| JP | 2004321612 | 11/2004 | |
| JP | 2005237608 | 9/2005 | |
| JP | 4210451 | 1/2009 | |
| JP | 2013008610 A | 1/2013 | |
| WO | WO 2005/112806 | 12/2005 | |
| WO | WO 2007/092636 | 8/2007 | |
| WO | WO 2008/033356 | 3/2008 | |
| WO | WO 2008/045374 | 4/2008 | |
| WO | WO 2008/061106 | 5/2008 | |
| WO | WO 2009/140288 A2 | 11/2009 | |
| WO | WO 2009/140288 A3 | 11/2009 | |
| WO | WO 2010/066789 | 6/2010 | |
| WO | WO 2010/066790 | 7/2010 | |
| WO | WO 2013/071938 | 5/2013 | |
| WO | WO 2013/106444 | 7/2013 | |
| WO | WO 2014/127780 | 8/2014 | |
| WO | WO 2016/188537 A1 | 12/2016 | |
| WO | WO 2016/188538 A1 | 12/2016 | |
| WO | WO-2016188539 A1 * | 12/2016 | ......... A61B 1/00142 |
| WO | WO 2017/167713 | 10/2017 | |

\* cited by examiner

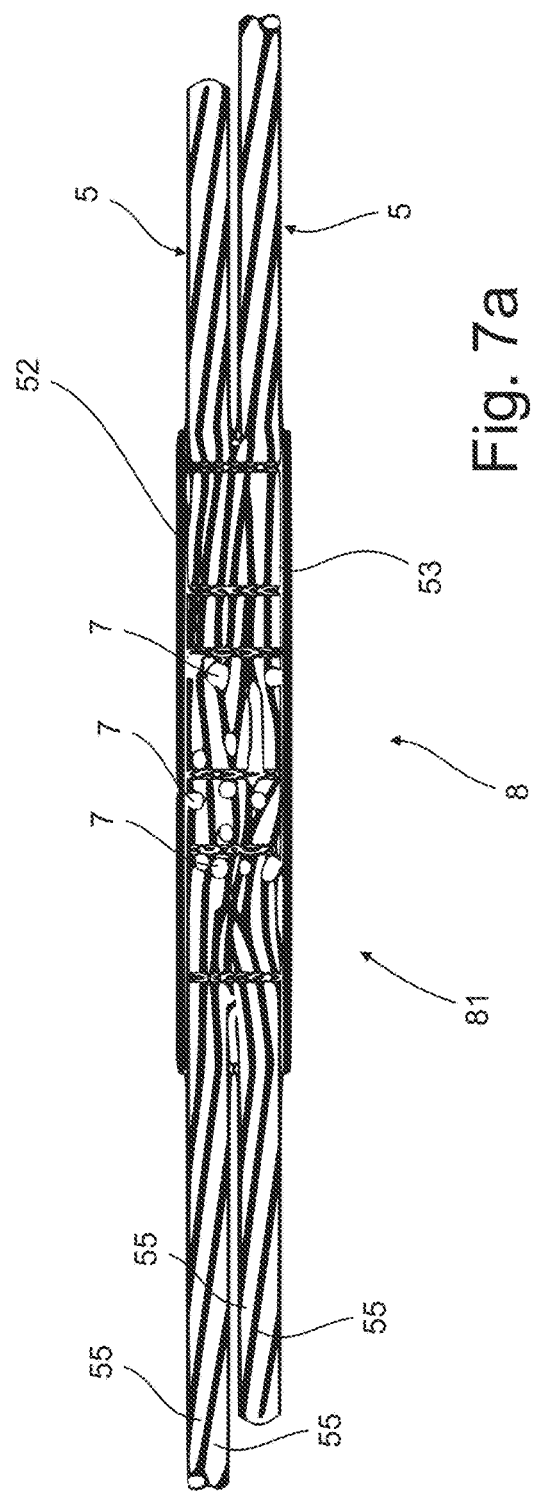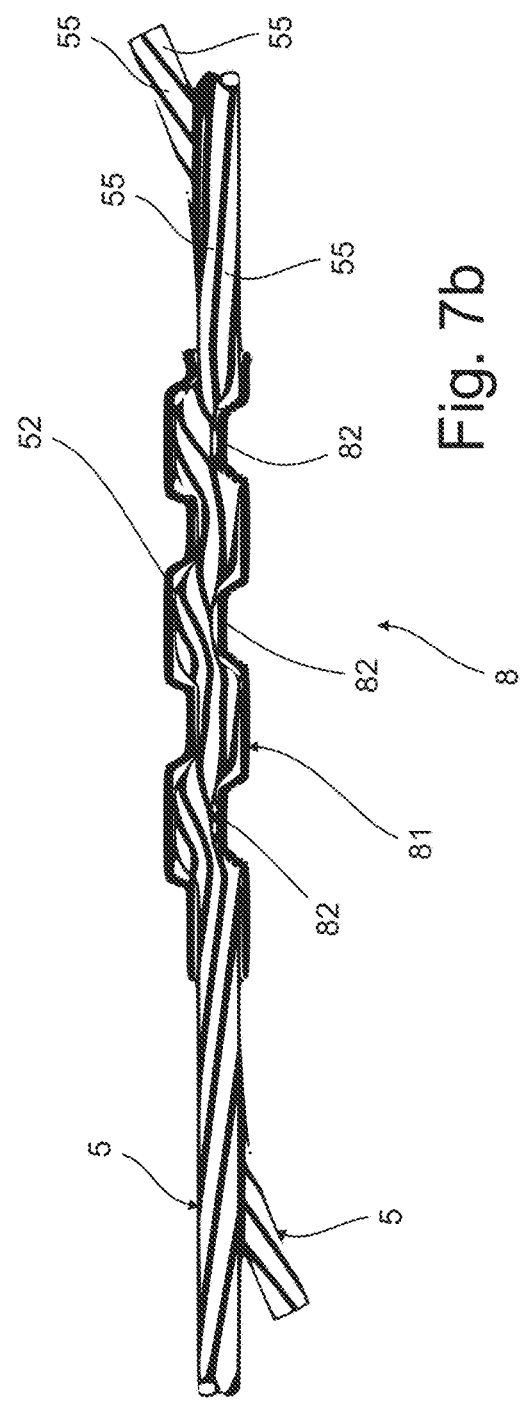

METHOD FOR FIXATION OF A WIRE PORTION OF AN ENDOSCOPE, AND AN ENDOSCOPE

CROSS-REFERENCE TO RELATED APPLICATIONS

This application claims the benefit of Europe Patent Application No. EP18152532.0, filed Jan. 19, 2018 and of Denmark Patent Application No. PA 2018 70530, filed Aug. 16, 2018. The foregoing patent applications are expressly incorporated herein by reference in their entirety.

TECHNICAL FIELD

The present disclosure relates to steerable endoscopes, and more specifically to a method for fixation of a steering wire.

BACKGROUND

Endoscopes are well known inspection devices. Generally, an endoscope comprises an insertion tube attached to a handle, and visual inspection means, such as a built-in camera, at a distal end of the endoscope. Electrical wiring for the camera and other electronics such as LED lighting typically runs along an inside of the insertion tube from the handle to the tip at the distal end. Instead of using cameras, endoscopes may also be fibre-optic, in which case optical fibres typically run along an inside of the insertion tube. A working channel may run along the inside of the insertion tube from the handle to the tip, e.g. allowing liquid to be removed from the body cavity or allowing for insertion of surgical instruments or the like into the body cavity.

In order to be able to maneuver a camera or the like of the endoscope inside the body cavity, the distal end of the endoscope may, in addition to the camera, comprise a section with increased flexibility, specifically an articulated or bendable tip allowing the operator to bend this section to thereby move the camera. Typically, maneuvering is carried out by tensioning or slacking steering wires in a guide tube also running along the inside of the elongated insertion tube from the articulated tip part to a control element with an operating member in the handle in an arrangement commonly known as a Bowden cable.

The steering wire running along the inside of the guide tube in a Bowden cable arrangement normally extends with a predetermined length over either end, allowing an operating member to be attached to a free (proximal) end of the wire, and an operated member to be attached to the other free (distal) end. When the ends of the guide tube are held stationary, movement of the proximal end of the steering wire with respect to the guide tube is transmitted to the distal end as a corresponding movement of the distal end of the steering wire with respect to the guide tube, so as to effect a movement of the operated member. The fastening of the proximal end of the guide tube to the operating handle is generally achieved with mechanical means where the guide tube is clamped, terminated in a block member, or adhered to the operating handle.

In order for the operator to have a good and responsive experience controlling the endoscope, the amount of play experienced by the operator during articulation of the steerable tip should be as small as possible. The amount of play may depend on many factors, including the tension and friction of the steering wire. To achieve a suitable tension of the steering wire, the wire is usually maintained in a pre-tensioned state. However, if the maintained tension of the steering wire is too high, the steerable tip may be non-straight, or mechanical parts of the endoscope may break. On the other hand, if the tension of the steering wire is too low, the steering wire will have too much play and be partly or wholly unresponsive to the control of the operator.

On this background, it is an object of the present invention to provide an improved endoscope, preferably a disposable endoscope. Another object of the present invention is to provide an improved method for fixation of a wire portion of an endoscope.

SUMMARY

It is an object of the present invention to provide an improved endoscope, preferably a disposable endoscope, and an improved method for fixation of a wire portion of an endoscope. In some embodiments, a method for fixation of a wire portion of an endoscope is provided, the method comprising: passing a steering wire through an insertion tube, the steering wire having a first wire portion, a second wire portion, a third wire portion and a fourth wire portion, the second wire portion being between the first wire portion and the third wire portion, and the third wire portion being between the second wire portion and the fourth wire portion; connecting the first wire portion of the steering wire to a steerable tip part of the endoscope; positioning the second wire portion adjacent the third wire portion; applying an adhesive on at least one of the second wire portion and the third wire portion; positioning the crimp shell in proximity of the second wire portion and the third wire portion with the crimp shell at least partly enclosing the adhesive, the second wire portion, and the third wire portion; and crimping the crimp shell to form a crimp securing the second wire portion to the third wire portion.

In some embodiments, an endoscope is provided, the endoscope comprising: an operating handle; an insertion tube with a proximal end and a distal end, and with a steerable tip part located at the distal end; a control element movable in relation to the operating handle; a steering wire having first, second, and third wire portions, the first wire portion being connected to the steerable tip part, and the second wire portion being located between the first and third wire portions; an adhesive on at least one surface of at least one of the second and third wire portions; and a crimp shell fixating and at least partly enclosing the second wire portion, the third wire portion, and at least a portion of the adhesive.

BRIEF DESCRIPTION OF THE DRAWINGS

Embodiments of the present disclosure will now be described, by way of example only, with reference to the accompanying drawings, in which:

FIG. 7a is a schematic cross-sectional view of a crimp shell after crimping;

FIG. 7b is another schematic cross-sectional view of the crimp shell of FIG. 7a.

DETAILED DESCRIPTION

Figure 1:
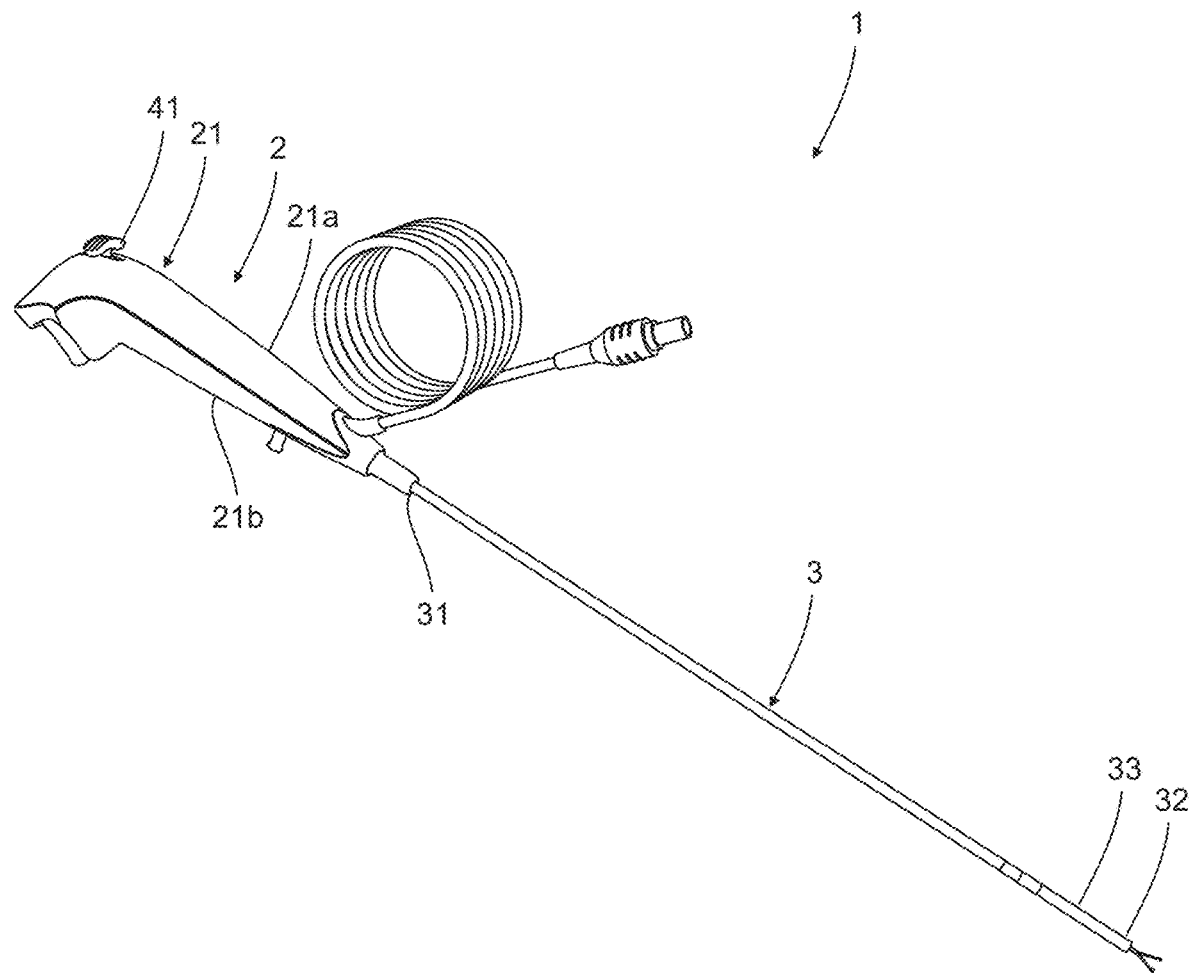
FIG. 1 is a perspective view of an endoscope.

The embodiments described below are merely exemplary and are not intended to limit the invention to the precise forms disclosed. Instead, the embodiments were selected for description to enable one of ordinary skill in the art to practice the invention.

In the prior art, steel has typically been employed as the steering wire material. A steel steering wire can achieve an adequate crimp yield strength combined with a tolerable amount of friction. It has been realized that, among other factors, the yield strength of the crimp depends on the friction of the wire, wherein a high friction of the wire provides a crimp with a high yield strength. The surface friction of steel steering wires is typically high, which results in a high crimp yield strength. However, a steel steering wire introduces a risk of providing an electrical connection between the operating handle and the steerable tip part of the insertion tube.

It has also been realized that the amount of friction of the steering wire and, thus, the amount of play depends on the friction between the steering wire and the guide tube or the like in which the steering wire is guided. As the friction of the steering wire increases, the amount of play also increases. In order to achieve a smooth controlling of the steerable tip part, it has therefore been realized that the coefficient of friction of the steering wire should be low. However, if using a wire of lower surface friction, the yield strength of the crimp may be reduced potentially to an inadequate level.

Surprisingly, it has been found that the method according to the invention may significantly increase a yield detachment force of the crimp joint, even with the use of adhesives of poor shear adhesion. Therefore, the method according to the invention may allow the use of a wider range of steering wire materials, including polymer plastics. Furthermore, the same tensioning method may be used as for steel steering wires. Additionally, tests have shown that the endoscope manufactured according to the invention may be resistant to aging, resulting in a satisfactory shelf life.

Advantageously, endoscopes made in accordance with the methods described herein may have more responsive and/or more precise steering mechanisms than prior endoscopes. In some embodiments, the steering wire comprises a plastic polymer which is crimped and adhesively bonded to increase a yield strength of the crimp, thereby enabling use of an electrically non-conductive, flexible steering wire with a low coefficient of friction while achieving a yield strength equivalent to that achieved with steel wire. Advantages are also obtained by the disclosed method using steering wires consisting of metal and other compositions.

The term "endoscope" as used herein is a device suitable for examination of spaces, including natural and/or artificial body openings, e.g. for exploration of a lung cavity. An endoscope may be a medical device. Examples of endoscopes include colonoscopes, bronchoscopes, gastroscopes, rhinolaryngoscopes and sigmoidoscopes, among other scopes. The insertion tube of the endoscope, or a distal end thereof, may be suitable for insertion into a body cavity, potentially a lung, through a body opening, potentially a mouth. The body may be a natural and/or artificial body, potentially a human body. The insertion tube may extend from the operating handle towards a distal end of the endoscope.

As used herein, the terms "distal" and "proximal" are relative to an operator of the endoscope, proximal being the end closest to the operator and distal being the end remote from the operator.

The term "steering wire" may be defined as an elongate member suitable for the purpose of controlling a steerable tip part by means of a control element, potentially as forming part of a cord drive or a Bowden cable arrangement for this purpose. The steering wire may further be tensionable. The term "steering wire" may include one or more from the group consisting of: a line, a cord, a thread, a string, a rope, a wire rope, a stranded wire rope, a cable, and a fishing line. Additionally or alternatively, the steering wire may be a monostranded, monofilament, multistranded or multifilament wire. A multistranded wire may also be known as a wire rope. In case of a multistranded wire, the strands may be braided, twisted, woven, coiled, or coiled wound.

The term (noun) "crimp" may be defined as a portion of a crimp shell which is deformed after applying a crimping force and/or as the crimp shell after having been deformed. As used herein, "crimp length" refers to a length of the crimp shell which has been crimped. The crimp length is potentially a fraction of the length of the crimp shell.

The term "partly enclosing" may alternatively be denoted as partly surrounding or partly covering.

When fixating the steering wire in an endoscope, it is desired to provide a crimp which can resist a sufficiently high detachment force. As used herein, "a detachment force" is the force attempting to break the attachment between the crimp and the wire by pulling a portion of the wire on one side of the crimp away from a portion of the wire on the other side of crimp. The "yield detachment force" is the detachment force required to break the attachment between the crimp and the wire. In the present specification, this is also denoted as the "yield strength" of the crimp.

A first aspect of the invention relates to a method for fixation of a wire portion of an endoscope. A second aspect of the invention relates to an endoscope. Referring to FIG. 1, an endoscope 1 according to an embodiment of the second aspect of the invention assembled by a method according to an embodiment of the first aspect of the invention is provided. The endoscope 1 comprises an operating handle 2, an insertion tube 3, and a control element 4, see also FIG. 2. The operating handle 2 is suitable for allowing an operator to grip and to operate the endoscope 1 with one hand. A handle housing 21, comprising two shells 21a, 21b, accommodates the control element 4.

The insertion tube 3 is an elongate member suitable for insertion into a patient, such as into a patient's lung through the patient's mouth. The insertion tube 3 extends from the operating handle 2 towards a distal end (to the right in FIG. 1) of the endoscope 1. The insertion tube 3 has a proximal end 31 connected to the handle housing and a distal end 32, and with a steerable tip part 33 located at the distal end 32.

Figure 2:
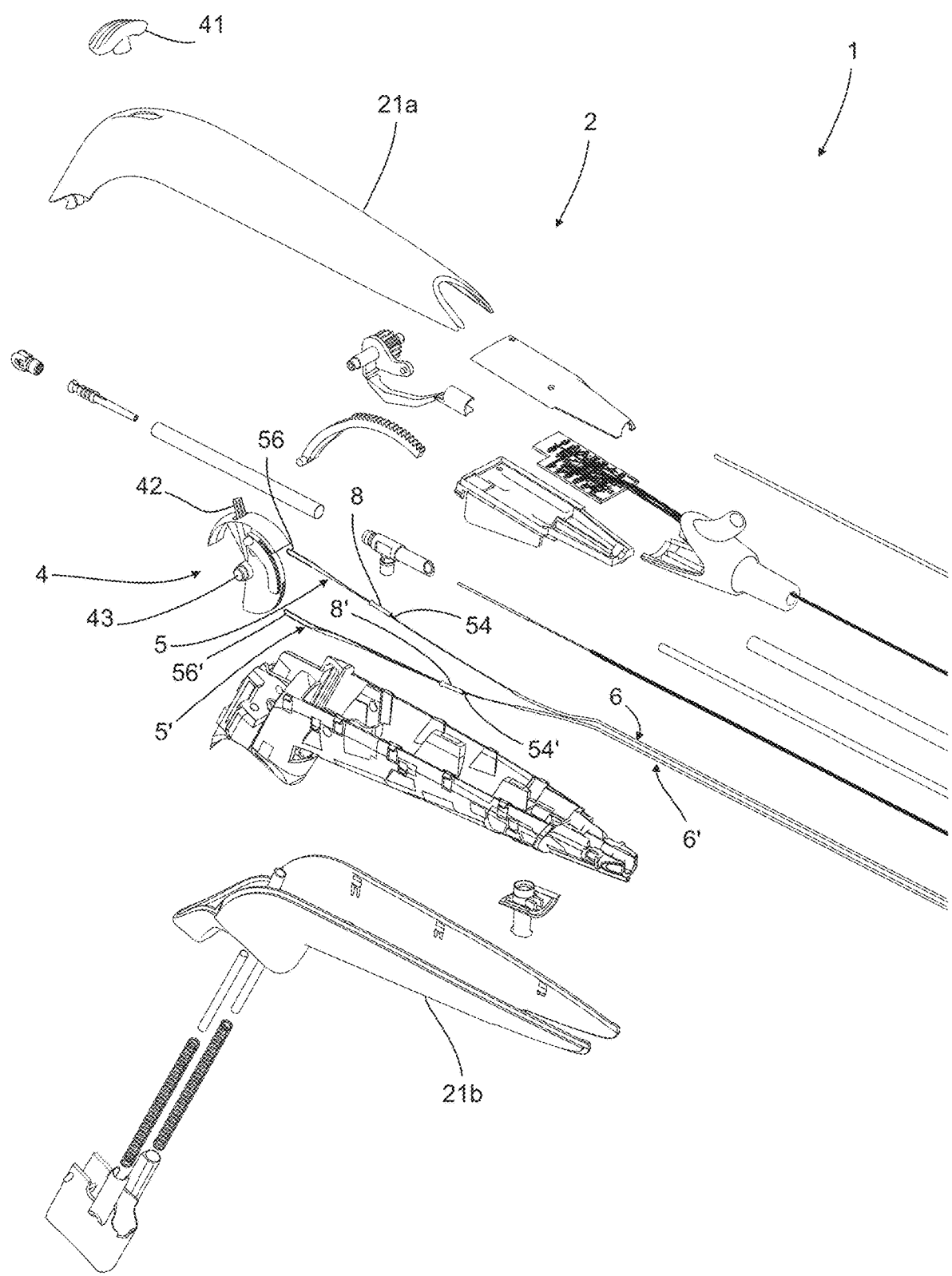
FIG. 2 is an exploded perspective view of the endoscope of FIG. 1.

The control element 4 is configured to allow an operator to control the steerable tip part 33 of the insertion tube 3 by two steering wires 5, 5', see also FIG. 2. The control element 4 allows bending the steerable tip part 33 in two directions. The control element 4 includes an operating member 41 allowing an operator to control the control element 4. The operating member 41 is connected to a lever 42 connected to and extending outwardly from the control element 4 through the handle housing 21 and is movable in relation to the operating handle 2. FIG. 2 shows a set of parts for the endoscope 1 from FIG. 1, further showing that the endoscope comprises a first 5 and a second 5' steering wire each respectively located in a first 6 and a second 6' wire support in the form of a respective first and a second guide tube. The apostrophe suffix of a reference number denotes an element associated with the second steering wire 5' corresponding to a similar element associated with the first steering wire 5, e.g. the first wire support 6 is associated with the first steering wire 5, and the second wire support 6' is associated with the second steering wire 5'.

In the present embodiment, each steering wire 5, 5' is an elongate, braided wire rope forming part of a Bowden cable arrangement for controlling the steerable tip part 33 by means of the control element 4. Each steering wire 5, 5' consists essentially of a plastic polymer in the form of ultra-high-molecular-weight polyethylene (UHMWPE) polymer. Each steering wire 5, 5' has a diameter of about 0.25 mm.

Each steering wire 5, 5' has a first (not shown); a second 52, 52'; a third 53, 53' and a fourth wire portion 54, 54'. Each of the first wire portions is connected to the steerable tip part 33. The wire portions are located in sequence first to third along each steering wire 5, 5' so that going from the first wire portion along the respective steering wire 5, 5', the next wire portion is the second wire portion 52, 52', then the third wire portion 53, 53', and lastly the fourth wire portion 54, 54', which terminates in a wire end.

Each steering wire 5, 5' extends from the second wire portion 52, 52', forms a loop 56, 56' and extends back in parallel to the second wire portion 52, 52' so that the second 52, 52' and third wire portions 53, 53' are located adjacently. An adhesive 7, 7' is applied on the second 52, 52' and third 53, 53' wire portions before the crimping action. Two crimp shells 8, 8' enclose the respective second 52, 52' and third 53, 53' wire portions.

In the endoscope assembled by the method according to the invention, the control element may be configured to allow an operator to control the steerable tip part of the insertion tube by the at least one steering wire. The control element may allow bending the steerable tip part in at least one direction, potentially in two directions, the two directions potentially being opposite. The control element may be accommodated in the operating handle. The control element may include a lever allowing an operator to control the control element. The lever may extend outwardly from the control element, potentially through the operating handle. The control element may be in the form of a roller or a roller disc.

As shown, the control element 4 has two wire guides (not shown): a first wire guide for accommodating the loop 56 of the first steering wire 5, and a second wire guide for accommodating the loop 56' of the second steering wire 5'. The lever 42 is attached to the roller or roller disc, having an axis 43, and allows an operator to rotate the control element 4 around the axis 43 in a known manner.

In the present embodiment, each crimp shell 8, 8' is an elongate and hollow member suitable for being crimped. Each crimp shell 8, 8' has a cylinder shell shape with an internal spacing configured to receive two portions of a steering wire 5, 5'. An outer contour of the cross-sectional shape of each of the crimp shells 8, 8' in a plane normal to the longitudinal axis thereof is round. The length of each of the crimp shells 8, 8' is approximately 10 mm. Each of the crimp shells 8, 8' essentially consists of steel.

An adhesive is used to bond portions of the steering wire. The adhesive may be applied as a liquid adhesive, especially a glue, and/or may be a reactive adhesive and/or a chemically curing adhesive, and/or may be converted from a liquid state to a solid state from a chemical reaction. Such chemical reaction may be initiated by heat, moisture, radiation and/or pressure. The adhesive may be a single component adhesive selected from the group consisting of: anaerobic, cyanoacrylate, heat hardenable, moisture hardenable, radiation hardenable and silicone adhesive. The cyanoacrylate adhesive may be an ethyl 2-cyanoacrylate adhesive, which is a reactive single component adhesive, that, when chemically cured, converts from a liquid state to a solid state by a chemical reaction initiated by moisture, in particular air humidity. The chemical reaction is also known as hardening or setting.

In some embodiments, the crimp shell may be a potentially elongate and/or hollow member suitable for being crimped. The crimp shell may have a tubular shape or a cylinder shell shape. The crimp shell may comprise a spacing configured to receive a portion, potentially two portions, of a steering wire therein. The two portions may overlap, as shown in FIG. 7. An outer contour of a cross-sectional shape of the crimp shell in a plane normal to the longitudinal axis thereof may be round or rounded, oval, triangular, ellipsoid, square, rectangular, polygonal, U-shaped; V-shaped, L-shaped, C-shaped or lens-shaped, wherein lens-shaped may be defined as the union of the intersection of two disks. The crimp shell may be open or partially open, e.g. comprising a slit extending along the longitudinal axis, or it may be circumferentially closed. The crimp shell may have a flared end on its proximal end, to prevent marring the wires.

A length of the crimp shell may be at least 2 mm, 3 mm, 5 mm, 6 mm or 7 mm. A length of the crimp shell may less than 30 mm, 25 mm, 20 mm, 17 mm or 15 mm. A length of the crimp shell may be 2-30 mm, 3-25 mm, 5-20 mm, 6-17 mm or 7-15 mm.

The crimp shell may comprise one or more materials selected from the group consisting of: metal, steel, aluminium, and titanium, polymer and plastic polymer. The crimp shell may consist essentially of a material selected from this group of materials.

Figure 3:
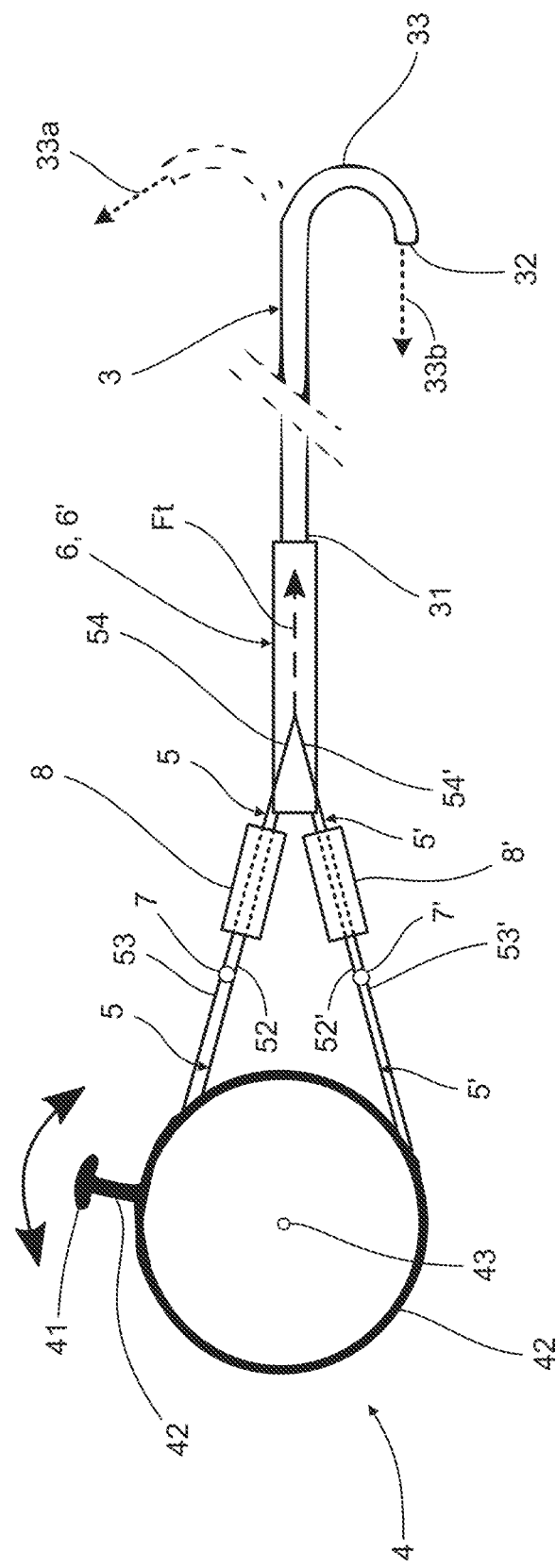
FIG. 3 is a side view schematically illustrating operation of a steerable tip part of an endoscope.
Figure 4A:
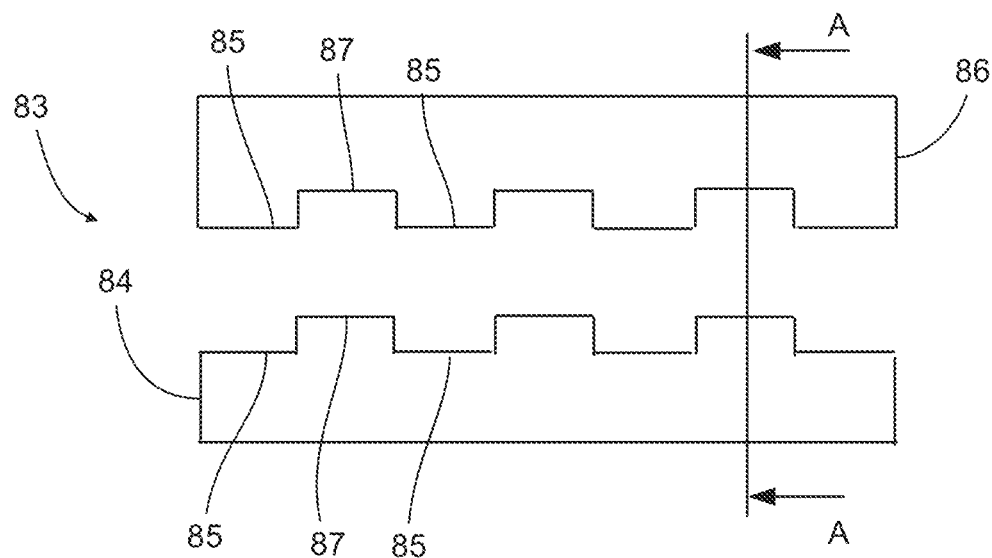
FIG. 4a is a schematic view of a crimping tool.
Figure 4B:
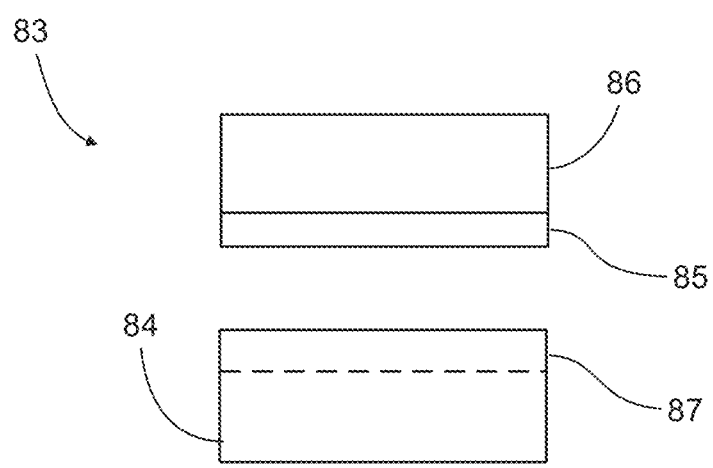
FIG. 4b is a schematic cross-sectional view of a crimping tool.
Figure 5:
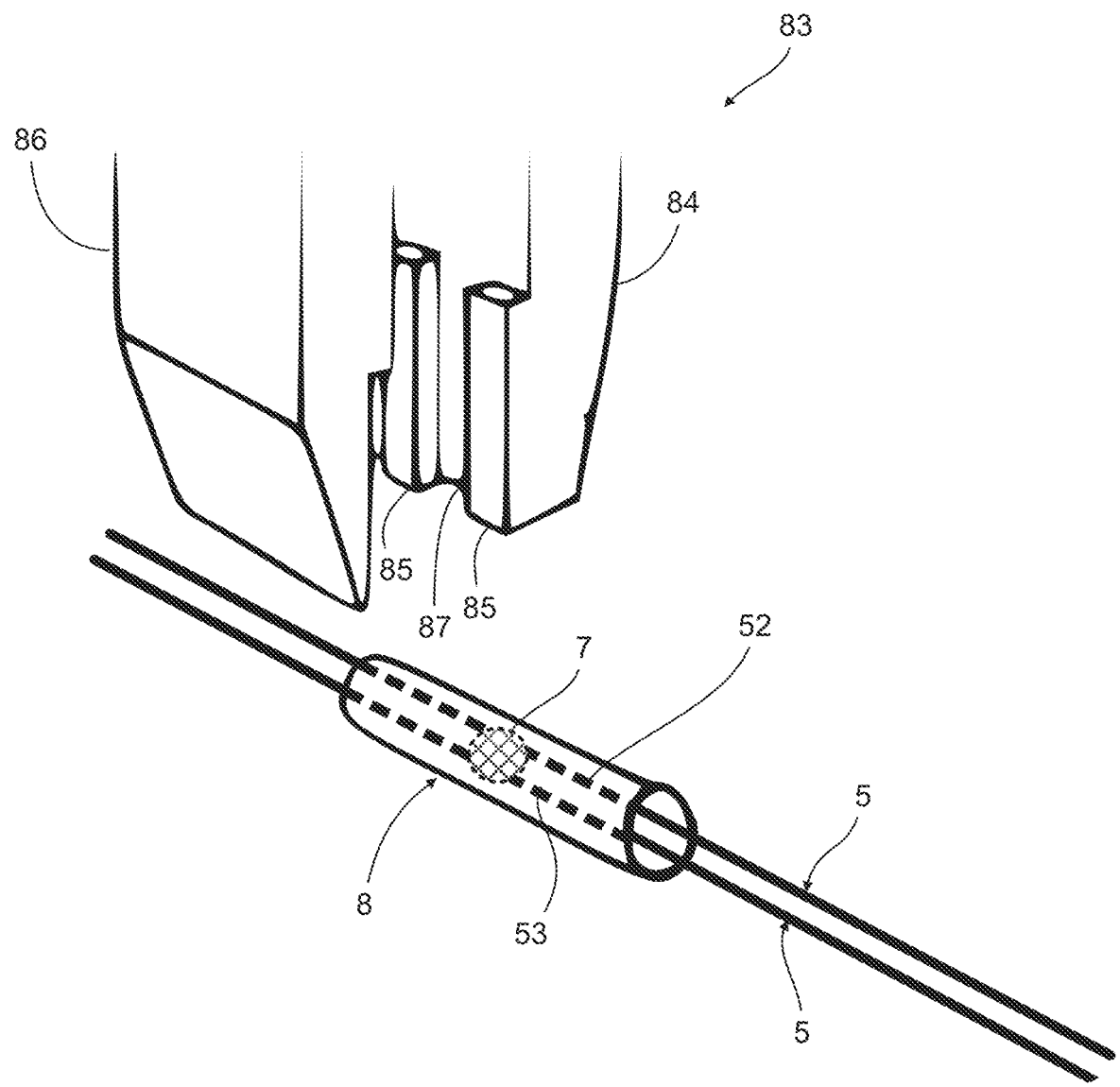
FIG. 5 is a schematic view of a crimping tool and a crimp shell prior to crimping with hidden lines shown as dashed lines.

FIGS. 3-5 show an embodiment of a method, according to the first aspect of the invention, of attaching two steering wires 5, 5' in the endoscope 1 so as to allow control of a steerable tip part 33 by activation of the control element 4. The method can be provided in a similar fashion for attaching a single steering wire. The guide tubes 6, 6' are schematically shown in FIG. 3 as a single guide tube which represents the two separate guide tubes 6, 6' shown in FIG. 2.

Still referring to FIG. 3, the present embodiment of the method of attaching two steering wires 5, 5' is carried out as follows:

First, the first steering wire 5 is attached to the steerable tip part 33 through the guide tube 6 so that, when pulled, the steerable tip part bends in a first direction 33a, which is shown in dashed lines in FIG. 3. The second steering wire 5' is attached to the steerable tip part 33 through the guide tube 6' so that, when pulled, the steerable tip part 33 bends in a second direction 33b, which is shown with solid lines in FIG. 3.

Second, the loops 56, 56' of the respective steering wires 5, 5' are positioned in their respective wire guides (not shown) in the control element 4. The second 52, 52' and third 53, 53' wire portions are then positioned adjacent to each other so that they extend in opposite and parallel directions.

Third, the fourth wire portions 54, 54' are pulled with a force Ft so as to tension the steering wires 5, 5' to a first wire tension between the first 51, 51' and the fourth wire portions 54, 54'. The tension of each wire is adjusted so that the steerable tip part 33 is straight.

Fourth, the adhesive 7, 7' is directly applied as a liquid adhesive droplet to a length of the second 52, 52' and third 53, 53' wire portions of each of the respective steering wires 5, 5'. This length is approximately four steering wire diameters or approximately 1 mm. The liquid adhesive is applied so that liquid adhesive is distributed between the strands 55, 55' of the second 52, 52' and third 53, 53' wire portions, which is shown in more detail in FIGS. 7a-b.

Referring to FIGS. 4a, 4b, and 5, a crimping tool 83 having a first tool part 84 and a second tool part 86 is positioned in a proximity to the crimp shell 8. FIG. 4b shows a cross-section A-A of the crimping tool 83 shown in FIG. 4a. The crimping tool 83 has a plurality of pairs of corresponding protrusions 85 and depressions 87, wherein the first tool part 84 comprises one of the corresponding protrusions 85 and depressions 87 of a pair and the second tool part 86 comprises the other one of the corresponding protrusions 85 and depressions 87 of the pair, and wherein the plurality of pairs are located alternately across each tool part 84, 86 so that a protrusion 85 has adjacent depressions 87 on each side and a depression 87 has adjacent protrusions 85 on each side.

Fifth, as shown in FIG. 5 for a single crimp shell 8, the crimp shell 8 is positioned in proximity of the second 52 and third 53 wire portions so that it encloses the second 52 and third 53 wire portions and the adhesive 7.

Figure 6:
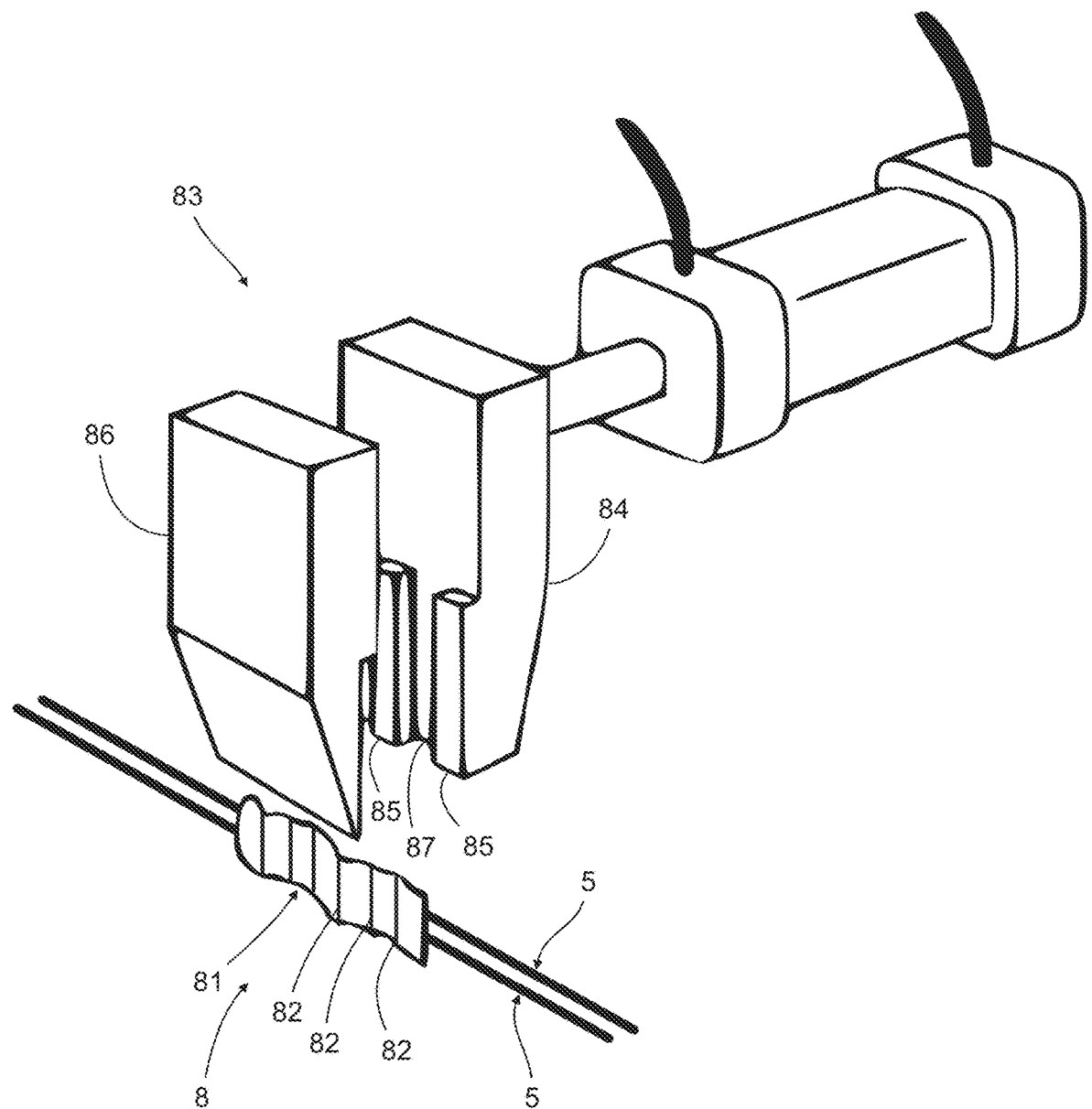
FIG. 6 is a view similar to that of FIG. 5 showing the crimp shell after crimping.

Sixth, with reference to FIG. 6, the crimping tool 83 is moved so that the crimp shell 8 is positioned between the first 84 and second 86 tool part. The first 84 and second 86 tool parts are then moved towards each other so that the tool parts 84, 86 abut the crimp shell 8 and then moved further, thereby applying a crimping force to compress the crimp shell 8 until the protrusion 85 of a pair protrude into the corresponding depression 87 of the pair so as to provide a crimp 81 fixating the second and third wire portions in relation to each other. The crimped crimp shell 8 encloses at least in part the second 52 and third 53 wire portions and the adhesive 7. The crimp 81 has a plurality of crimp deformities 82, each formed by one pair of protrusion 85 and depression 87. This is seen in FIG. 6 for a single crimp shell 8, a similar method may be applied for the second crimp shell 8'. The crimp 81 is the portion of the crimp shell 8 which is deformed after applying the crimping force.

Seventh, the adhesive 7 is allowed to harden so as to maintain the tension of the wire 5 in a second wire tension. The second wire tension is substantially the same as the first wire tension.

A crimp shell 8 with a crimp 81 enclosing a second 52 and a third 53 wire portion of a single steering wire 5 manufactured according to the above method is shown in FIGS. 7a and 7b. The second wire portion 52 is positioned above the third wire portion 53, and droplets of the adhesive 7 are located and distributed between strands 55 of the steering wire inside the crimp. The adhesive 7 is positioned so that it adheres:
  the second 52 and third 53 wire portions to each other; and
  a plurality of strands of both the second 52 and third 53 wire portions to each other; and
  the crimp 81 to the second wire portion 52 and the crimp 81 to the third wire portion 53.

The steering wire may comprise a metal, potentially steel. The steering wire may comprise, preferably consist essentially of, a polymer or plastic polymer or a combination of polymers suitable for being used as a wire. Alternatively or additionally, the steering wire may comprise one or more materials selected from the group consisting of: metal, steel, carbon steel, non-alloy carbon steel, non-alloy carbon steel with a carbon content of 0.3% to 1%, a polymer, a plastic polymer, polyethylene (PE), polyimide (PA), polyamide-imides (PAI), ultra-high-molecular-weight polyethylene (UHMWPE), high-density polyethylene (HDPE), low-density polyethylene (LDPE), high-molecular-weight polyethylene (HMWPE), natural fibres, artificial fibres, glass fibres, and carbon fibres. In case of plastic polymers, such as PE, the fibres may be gel-spun. A plastic polymer may be defined as a synthetic malleable polymer, e.g. PE. Examples of suitable wires include wires comprising fibres traded under the trademarks Dyneema® and Honeywell Spectra®. The steering wire may consist essentially of one or more of the above mentioned materials. At least one, at least a quarter of, a majority of or all of or essentially all of the strands may consist essentially of one or more of the above mentioned materials.

The material of the steering wire may have a dry static coefficient of friction lower than 0.5, 0.45 or 0.4. Additionally, or alternatively, the material of the steering wire may have a dry dynamic coefficient of friction lower than 0.4, 0.35 or 0.3. The coefficient of friction may be measured in relation to the same material.

The steering wire may be less than 1 mm, 0.75 mm, 0.60 mm, 0.40 mm or 0.30 mm in diameter.

The third and fourth wire portions of the steering wire may be coinciding with each other or may be one and the same wire portion. Alternatively, the third and fourth wire portions of the steering wire may be provided separately or located at a distance from each other.

The steering wire may be a multistranded wire or wire rope. The steering wire may comprise at least 5, 10, 30, 100 or 1000 strands. The wire may be braided, twisted, woven, coiled, or coiled wound. This may decrease elasticity of the steering wire, which may be desirable since it may reduce the amount of play experienced by an operator and may increase the fatigue resistance of the crimp, prolonging the working life of the endoscope.

An advantage of using a steering wire of polymer material may be that polymer materials, compared to steel, may have a lower electrical conductivity and may have a lower coefficient of friction. By using a steering wire with a low or no electrical conductivity, it is easier to provide a configuration of an endoscope that meets the desirable electrical safety requirements. By providing a lower coefficient of friction, the resistance to movement, when controlling the endoscope using the control element, may be reduced, which may ensure a smoother operation of the endoscope.

However, using a polymer steering wire with a low coefficient of friction may present a challenge since the steering wire is attached to itself by a crimp, which may essentially be defined as a friction joint, and the detachment force may generally decrease when reducing the friction coefficient. In spite of this, and as mentioned above, applying adhesive to the crimp joint has been shown to increase the detachment force of the crimp, especially when using a polymer steering wire, potentially to levels above a crimp with a steel steering wire without an adhesive, see further below. Especially in the case of stranded wires, it is currently theorised that this technical effect is achieved by increasing the stiffness of the portion of the steering wire located in the crimp so that an attempt to break the crimp joint by pulling a wire portion on one side of the crimp away from a wire portion on the other side of the crimp is resisted by having a relatively stiff wire portion which does not easily flex to fit a crimp deformity of the crimp. Particularly when the adhesive sets in a deformity, pulling the wire from the crimp would require pulling the hardened deformed wire portion through the corresponding deformed crimp shell portion, and this requires more force than if the wire were not hardened or deformed.

Experiments show that the yield strength of a crimp is especially increased when the steering wire comprises strands. It is currently theorised that applying the adhesive so that the adhesive is distributed and hardened in between strands increases the local stiffness of the wire. This may ensure that, if the wire is subject to a detachment force, the local stiffness of the wire will increase the yield detachment force of the crimp, and thereby increase the yield strength of the crimp.

The crimp and the adhesive in conjunction may fixate or both contribute to the fixation of the second and third wire portions in relation to each other.

In some embodiments, the adhesive is a single component, anaerobic, cyanoacrylate, heat hardenable, moisture hardenable, radiation hardenable, and/or silicone adhesive.

In some embodiments, the crimp comprises at least one crimp deformity. A crimp deformity may be defined as the section of material deformed by a pair of a protrusion and a depression of a crimping tool. The crimp may comprise at least two, three or four crimp deformities. The crimping tool may comprise at least the same number of pairs of protrusions and depressions as the number of crimp deformities.

In some embodiments, the steering wire comprises a polymer, potentially a plastic polymer.

In some embodiments, the steering wire comprises at least two strands. The strands may be provided similarly as in the embodiments of the first aspect of the invention relating to strands, see above.

In some embodiments, two or more of the strands of the steering wire are braided and/or woven and/or twisted. This may decrease the elasticity of the steering wire, which may correspond to a reduction in elongation under the same loading. This is desirable since it reduces the amount of play experienced by an operator.

In some embodiments, at least part of the adhesive is located at least between at least two strands of at least one of the second and third wire portions. This may increase stiffness of steering wire in crimp and therefore increases detachment force required to break the crimp.

EXAMPLES

Figure 8:
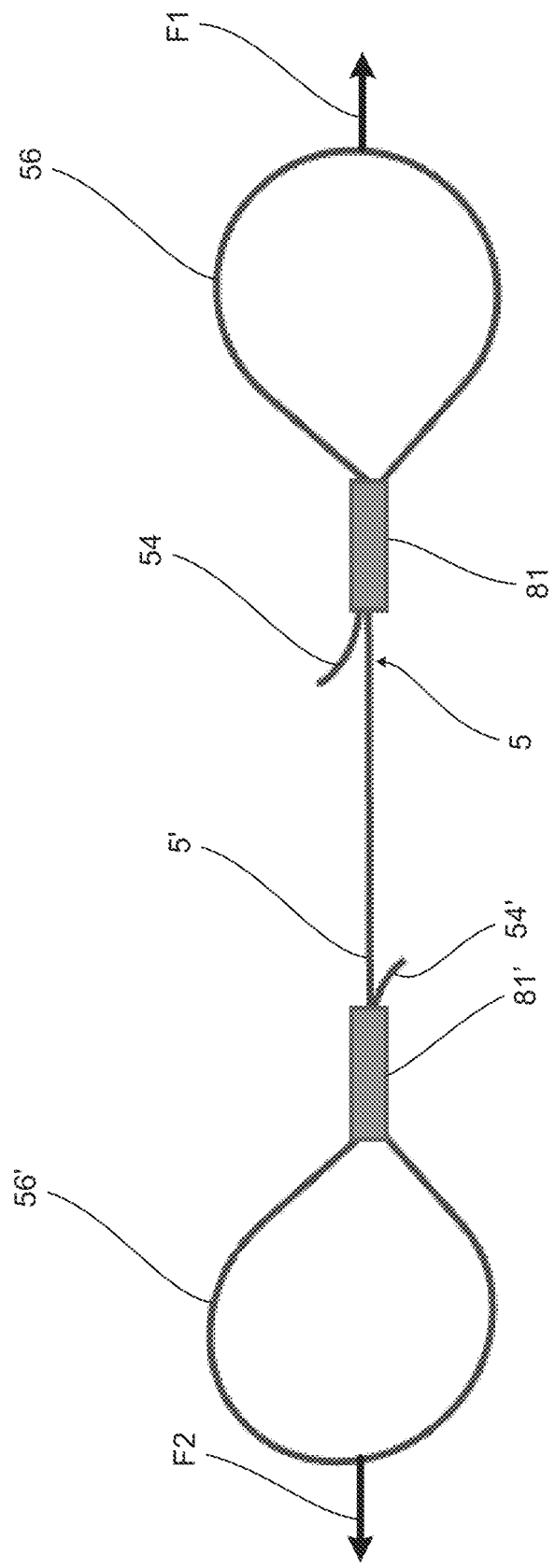
FIG. 8 is a schematic view of a test setup for testing a yield detachment force of a crimp.

Experiments to measure the yield detachment force of a crimp were conducted. A number of test samples were tested in a configuration shown in FIG. 8. One test sample comprised a single steering wire with a right half 5 forming a right loop 56 defining a right eye and a left half 5' forming a left loop 56' defining a left eye. The right 5 and left 5' halves of the steering wire were crimped according to the method described in connection with FIG. 3 at a right crimp 81 and at a left crimp 81' applying cyanoacrylate as adhesive within the crimps 81, 81' as described above.

Test samples comprising a steel wire and a polymer wire were tested. Table 1 below describes the items used.

TABLE 1

| List of items | |
|---|---|
| ITEM | DESCRIPTION |
| Steering wire-Steel | 402037, Ø0.25 |
| Steering wire-Polymer (UHMWPE) | RonThomsen-Hyperstrong, Ø0.25 |
| Crimp Shell | F75-10-M Ferrule distributed by Panduit, 888402043 |
| Adhesive | Cyanoacrylate (CA) glue Dana Lim A/S, Gelé 359 |

The yield detachment force of the crimp and wire was measured by applying a first pulling force F1 to the right eye of the test sample and a second pulling force F2 to the left eye of the test sample. The first F1 and second F2 pulling forces extended in parallel and opposite directions. The speed used to pull the test sample apart was 25 mm/min. The detachment force was then measured. Four experiments were conducted with 8-12 repetitions for each experiment. The yield detachment force in Newtons (N) for each repetition in these experiments are listed in Tables 2 and 3 below. Each row corresponds to a single repetition of the respective experiment. The bottom row is the average result of all repetitions for that experiment.

The variables in the experiments are whether adhesive is applied or not and the material of the steering wire.

The first and second experiments shown in Table 2 were conducted using a steel steering wire, wherein the first experiment is the steel wire 5, 5' without adhesive in the crimps 81, 81', and wherein the second experiment is the same type of steel wire with hardened cyanoacrylate adhesive in the crimps 81, 81'.

TABLE 2

Columns 1 and 2 relate to the experiments with a steel wire and without adhesive in the crimp. Columns 3 and 4 relate to the experiments with a steel wire and with cyanoacrylate (CA) adhesive in the crimp.

| ID | WITHOUT CA GLUE [N] | ID | WITH CA GLUE [N] |
|---|---|---|---|
| 1 | 45 | 1 | 59 |
| 2 | 43 | 2 | 57 |
| 3 | 45 | 3 | 57 |
| 4 | 55 | 4 | 57 |
| 5 | 44 | 5 | 57 |
| 6 | 28 | 6 | 58 |
| 7 | 28 | 7 | 56 |
| 8 | 33 | 8 | 58 |
| 9 | 53 | | |
| 10 | 38 | | |
| Average | 41N | | 57N |

The third and fourth experiments shown in Table 3 were conducted using a polymer steering wire, in particular a braided ultra-high-molecular-weight polyethylene (UHMWPE) wire rope. The third experiment is the same type of polymer wire rope 5, 5' without adhesive in the crimps 81, 81'. The fourth experiment is the same type of polymer wire rope 5, 5' as the previous experiment, this time with hardened cyanoacrylate adhesive in the crimps 81, 81'.

TABLE 3

Columns 1 and 2 relate to the experiments with a braided UHMWPE wire rope and without adhesive in the crimp. Columns 3 and 4 relate to the experiments with the same type of braided UHMWPE wire rope and with cyanoacrylate (CA) adhesive in the crimps.

| ID | WITHOUT CA GLUE [N] | ID | WITH CA GLUE [N] |
|---|---|---|---|
| 1 | 18 | 1 | 55 |
| 2 | 16 | 2 | 60 |
| 3 | 17 | 3 | 64 |
| 4 | 19 | 4 | 65 |
| 5 | 18 | 5 | 60 |
| 6 | 17 | 6 | 56 |
| 7 | 21 | 7 | 58 |
| 8 | 16 | 8 | 64 |
| 9 | 15 | 9 | 59 |
| 10 | 19 | | |
| 11 | 24 | | |
| 12 | 17 | | |
| Average | 18N | | 60N |

In Table 4 below, the results are summarized. From these results it is seen that the yield detachment force is surprisingly increased when applying adhesive to the crimp. This effect is extremely pronounced for the polymer wire, where the experiments show that the yield detachment force more than triples when using the adhesive. In fact, the yield detachment force for the polymer wire using adhesive is greater than the yield detachment force of the steel wire, both with and without adhesive.

TABLE 4

Yield detachment force increase in newtons in column 2, and in percentage in column 3, for the steel wire in row 2 and polymer wire in row 3. Results based on the experiments of Tables 2 and 3.

| STEERING WIRE MATERIAL | DETACHMENT FORCE STRENGTH INCREASE WITH CA GLUE [N] | DETACHMENT FORCE STRENGTH INCREASE WITH CA GLUE [%] |
|---|---|---|
| Steel | +16N | +39% |
| Polymer | +42N | +233% |

The crimp pattern, crimping force and amount, the amount of adhesive, and the thickness and construction of the steering wire can be selected to achieve a desirable yield detachment force. In one embodiment, the steering wire comprises a plastic polymer, the adhesive is hardenable or settable, and the yield detachment force after hardening or setting of the adhesive is greater than about 40 N. In another embodiment, he adhesive is hardenable or settable, and the yield detachment force after hardening or setting of the adhesive is greater than about 50 N. In another embodiment, the adhesive is hardenable or settable, and the yield detachment force after hardening or setting of the adhesive is between about 40-70 N, and more preferably between about 50-65 N.

List of reference numerals:

| NUMERAL | DESCRIPTION |
|---|---|
| 1 | endoscope |
| 2 | operating handle |
| 21 | handle housing |
| 3 | insertion tube |
| 31 | proximal end |
| 32 | distl end |
| 33 | steerable tip part |
| 33a | first direction |
| 33b | second direction |
| 4 | control element |
| 41 | operating member |
| 42 | lever |
| 43 | axis |
| 5 | steering wire |
| 51 | first wire portion |
| 52 | second wire portion |
| 53 | third wire portion |
| 54 | fourth wire portion |
| 55 | strand |
| 56 | loop |
| 6 | wire support |
| 7 | adhesive |
| 8 | crimp shell |
| 81 | crimp |
| 82 | crimp deformity |
| 83 | crimping tool |
| 84 | male tool part |
| 85 | protrusion |
| 86 | female tool part |
| 87 | depression |

Additional embodiments are disclosed below. In one embodiment according to the first aspect of the invention, the method for fixation of a wire portion of an endoscope comprises the steps of:
a) providing:
an operating handle;
an insertion tube with a proximal end and a distal end, and with a steerable tip part located at the distal end;
a control element movable in relation to the operating handle;
a steering wire having a first, a second, a third, and a fourth wire portion, the first wire portion being connected to the steerable tip part, the second wire portion being located between the first and third wire portions, the third wire portion being located between the second and fourth wire portions; and
a crimp shell;
b) pulling the fourth wire portion so as to tension the steering wire;
c) positioning the second and third wire portions adjacent to each other;
d) applying an adhesive on at least one of the second and third wire portions;
e) positioning the crimp shell in a proximity of the second and third wire portions; and
f) subsequent to steps c), d), and e), applying a crimping force to the crimp shell so as to provide a crimp fixating the second and third wire portions in relation to each other, the crimp at least partly enclosing at least a portion of the adhesive.

The method according to the first aspect of the invention may alternatively be provided as a method for fixation of a wire portion in a set of parts for an endoscope, the method comprising the steps of:
a) providing:
an operating handle;

an insertion tube with a proximal end and a distal end, and with a steerable tip part located at the distal end;
a control element movable in relation to the operating handle;
a steering wire having a first, a second, a third, and a fourth wire portion, the first wire portion being connected to the steerable tip part, the second wire portion being located between the first and third wire portions, the third wire portion being located between the second and fourth wire portions; and
a crimp shell;
b) pulling the fourth wire portion so as to tension the steering wire;
c) positioning the second and third wire portions adjacent to each other;
d) applying an adhesive on at least one of the second and third wire portions;
e) positioning the crimp shell in a proximity of the second and third wire portions; and
f) subsequent to steps c) and d), applying a crimping force to the crimp shell so as to provide a crimp fixating the second and third wire portions in relation to each other, the crimp at least partly enclosing at least a portion of the adhesive.

The method according to the first aspect of the invention may alternatively as a method for fixation of a wire portion of an endoscope, the method comprising the steps of:
a) providing:
an operating handle;
an insertion tube with a proximal end and a distal end, and with a steerable tip part located at the distal end;
a control element movable in relation to the operating handle;
a steering wire having a first, a second, a third, and a fourth wire portion, the first wire portion being connected to the steerable tip part, the second wire portion being located between the first and third wire portions, the third wire portion being located between the second and fourth wire portions; and
an attachment member;
c) positioning the second and third wire portions adjacent to each other;
d) applying an adhesive on at least one of the second and third wire portions;
e) positioning the attachment member in a proximity of the second and third wire portions; and
f) subsequent to steps c), d), and e), applying the attachment member fixating the second and third wire portions in relation to each other, the attachment member at least partly enclosing at least a portion of the adhesive.

The method according to the first aspect of the invention may alternatively be provided as a method for fixation of a wire portion in a set of parts for an endoscope, the method comprising the steps of:
a) providing:
an operating handle;
an insertion tube with a proximal end and a distal end, and with a steerable tip part located at the distal end;
a control element movable in relation to the operating handle;
a steering wire having a first, a second, a third, and a fourth wire portion, the first wire portion being connected to the steerable tip part, the second wire portion being located between the first and third wire portions, the third wire portion being located between the second and fourth wire portions; and
an attachment member;
c) positioning the second and third wire portions adjacent to each other;
d) applying an adhesive on at least one of the second and third wire portions;
e) positioning the attachment member in a proximity of the second and third wire portions; and
f) subsequent to steps c) and d), applying an attachment member fixating the second and third wire portions in relation to each other, the attachment member at least partly enclosing at least a portion of the adhesive.

During step b) of the method according to the first aspect of the invention, the wire may be tensioned to a first wire tension, and after step f) and/or step g) the tension of the wire may be maintained at a second wire tension. The first wire tension may be substantially the same as the second wire tension. Alternatively, the first and second wire tensions are different from each other.

In the method according to the first aspect of the invention, step b) may comprise pulling the fourth wire portion so as to tension the steering wire potentially between the first and third wire portions.

Step c) may comprise positioning the steering wire around a wire guide so that the third wire portion is positioned adjacent to the second wire portion.

The second and third wire portions may be positioned adjacent to each other so that they extend substantially in parallel.

The second and third wire portions may be positioned so that they extend in opposite, potentially parallel, directions Step d) may comprise applying the adhesive on at least one of the second and third wire portions through an opening or through-hole, potentially a lateral opening or through-hole, of the crimp shell.

Step d) may comprise applying the adhesive directly on at least one of the second and third wire portions.

Step d) may comprise applying the adhesive indirectly on at least one of the second and third wire portions, potentially by applying the adhesive to the crimp shell, potentially to the inside of the crimp shell, and then optionally positioning the crimp shell in a proximity of the second and third wire portions.

Step d) may be performed before step e).

Step e) may comprise positioning the crimp shell in a proximity of the second and third wire portions so that the crimp shell at least partly encloses the second and third wire portions.

Step e) may comprise positioning the crimp shell in a proximity of the second and third wire portions so that the crimp shell abuts at least one of the second and third wire portions. The term "partly enclosing" in step f) may alternatively be denoted as partly surrounding or partly covering.

Step f) may comprise positioning the crimp shell between a first and a second tool part, and then moving the first and second tool part towards each other, whereby a crimping force is applied to the crimp shell so as to provide a crimp fixating the second and third wire portions in relation to each other, the crimp at least partly enclosing at least a portion of the adhesive.

Step f) may comprise applying a crimping force to the crimp shell by heating or cooling the crimp shell so as to provide a crimp fixating the second and third wire portions in relation to each other, the crimp at least partly enclosing at least a portion of the adhesive. The crimp shell may comprise a heat-shrinkable material or a cold-shrinkable material.

The crimp may fixate the second and third wire portions to each other and/or fixate the second and/or third wire portions to the crimp shell.

In step e) and/or step f) the crimp may at least partly enclose the second and third wire portions.

The steps of the method according to the first aspect of the invention may be performed sequentially, potentially in the order a), b), c), d), e), f); in the order a), c), b), d), e), f); in the order a), b), c), e), d), f); or in the order a), c), b), e), d), f). However, the steps a)-e) are not necessarily performed in sequence, for instance step a) may be performed during step b) and/or step c).

In some embodiments of the method according to the first aspect of the invention, the adhesive is hardenable or settable, the method further comprising the step of: g) allowing the adhesive to harden or set. Preferably, step g) is performed after step f).

In some embodiments, the method further comprises the step of: h) releasing the fourth wire portion.

Step h) may be performed after step f), preferably after steps f)-g). Step h) may be performed after step a)-f), preferably after step a)-g). In step b) of the method, the pulling may be achieved by applying a pulling force to the fourth wire portion, and in step h) the pulling force may be released.

In some embodiments, the steering wire comprises at least two strands, wherein step d) of the method comprises applying the adhesive on at least one of the second and third wire portions so that the adhesive is distributed between at least two strands of the second and/or third wire portion(s). A "strand" may be defined as a wire strand. Additionally, or alternatively, a "strand" may be defined as a slender, thread-like line of material suitable for the purpose of being connected with other strands, potentially by braiding, twisting, weaving, coiling or coiled winding, to form a wire.

In some embodiments, the step d) of the method according to the first aspect of the invention comprises applying the adhesive as a liquid adhesive, optionally as a droplet, optionally on at least one of the second and third wire portions. This may have the advantage of increasing the stiffness of the wire, which in turn may increase the detachment force of the crimp joint.

Additionally, or alternatively, step d) of the method comprises applying a volume of the adhesive as a liquid adhesive, optionally as a droplet, on at least one of the second and third wire portions, the volume optionally being 0.001 mL-1 mL, 0.005 mL-0.5 mL, 0.0075 mL-0.25 mL or 0.01 mL-0.1 mL.

In some embodiments, the step d) of the method according to the first aspect of the invention comprises distributing the adhesive on a length of at least one of the second and third wire portions, the length being equal to or above a diameter or a cross-sectional width of the steering wire. This may have the advantage of increasing the stiffness of the wire, which, in turn, may increase the detachment force of the crimp joint. Alternatively, or additionally, the length may be equal to at least a fifth of the crimp length, a quarter of crimp length, half the crimp length or the crimp length. Alternatively, or additionally, the length may be at least 1 mm, 2 mm, 3 mm, 4 mm or 5 mm.

In some embodiments, the step d) of the method according to the first aspect of the invention comprises at least applying the adhesive on the second and third wire portions at least partly between the second and third wire portions. This may have the advantage of increasing the stiffness of the wire, which, in turn, may increase the detachment force of the crimp joint. The step d) may comprise at least applying the adhesive on the second and third wire portions at least partly between the second and third wire portions.

In some embodiments, the step a) of the method according to the first aspect of the invention further comprises the step of:

providing a crimping tool comprising a first and a second tool part, the first tool part optionally including at least one protrusion, and/or the second tool optionally including at least one depression preferably corresponding to the at least one protrusion of the first tool part; and wherein, optionally, in step e) the crimping tool further applies the crimping force by compressing, potentially opposite, sides of the crimp shell so as to provide a crimp fixating the second and third wire portions in relation to each other, the crimp at least partly enclosing the second and third wire portions and at least a portion of the adhesive.

Step e) may comprise positioning the crimp shell between the first and second tool parts, and then apply the crimping force by optionally moving the first and second tool part towards each other, whereby the protrusion of the first tool part is moved into a depression of the second tool part so as to provide a crimp fixating the second and third wire portions in relation to each other, the crimp at least partly enclosing the second and third wire portions and at least a portion of the adhesive.

The second aspect of the invention relates to an endoscope comprising:
- an operating handle;
- an insertion tube with a proximal end and a distal end, and with a steerable tip part located at the distal end;
- a control element movable in relation to the operating handle;
- a steering wire having first, second, and third wire portions, the first wire portion being connected to the steerable tip part, the second wire portion being located between the first and third wire portions;
- an adhesive provided on at least one surface of at least one of the second and third wire portions; and
- a crimped crimp shell forming a crimp at least partly enclosing the second wire portion, the third wire portion, and at least a portion of the adhesive.

The endoscope according to the second aspect of the invention may alternatively be provided as an endoscope comprising:
- an operating handle;
- an insertion tube with a proximal end and a distal end, and with a steerable tip part located at the distal end;
- a control element movable in relation to the operating handle;
- a steering wire having first, second, and third wire portions, the first wire portion being connected to the steerable tip part, the second wire portion being located between the first and third wire portions;
- an adhesive provided on at least one surface of at least one of the second and third wire portions; and
- an attached attachment member fixating and at least partly enclosing the second wire portion, the third wire portion, and at least a portion of the adhesive.

The endoscope according to the second aspect of the invention may be manufactured by means of the first aspect of the invention.

The endoscope according to the second aspect of the invention may alternatively be provided as a set of parts for an endoscope, the set of parts comprising:
- an operating handle;
- an insertion tube with a proximal end and a distal end, and with a steerable tip part located at the distal end;

a control element movable in relation to the operating handle;

a steering wire having first, second, and third wire portions, the first wire portion being connected to the steerable tip part, the second wire portion being located between the first and third wire portions;

an adhesive provided on at least one surface of at least one of the second and third wire portions; and a crimped crimp shell forming a crimp at least partly enclosing the second wire portion, the third wire portion, and at least a portion of the adhesive.

The endoscope according to the second aspect of the invention may alternatively be provided as a set of parts for an endoscope, the set of parts comprising:

an operating handle;

an insertion tube with a proximal end and a distal end, and with a steerable tip part located at the distal end;

a control element movable in relation to the operating handle;

a steering wire having first, second, and third wire portions, the first wire portion being connected to the steerable tip part, the second wire portion being located between the first and third wire portions;

an adhesive provided on at least one surface of at least one of the second and third wire portions; and an attached attachment member fixating and at least partly enclosing the second wire portion, the third wire portion, and at least a portion of the adhesive.

In some embodiments of the endoscope according to the second aspect of the invention, the adhesive is provided so as to adhere:

the crimp to at least one of the second and third wire portions; and/or the second and third wire portions to each other; and/or at least two strands of one of the second and third wire portions to each other; and/or the crimp to the second wire portion and/or the crimp to the third wire portion.

Any one or more of the embodiments relating to the first or second aspect of the invention may be combined with any one or more of the embodiments relating to either the same aspect of a different aspect.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:

1. A method for fixation of a wire portion of an endoscope, the method comprising:

passing a steering wire through an insertion tube, the insertion tube having a proximal end and a distal end, the proximal end connected to an operating handle of the endoscope including a control element movable in relation to the operating handle, the steering wire comprising a stranded plastic polymer having a first wire portion, a second wire portion, a third wire portion and a fourth wire portion, the second wire portion being between the first wire portion and the third wire portion, and the third wire portion being between the second wire portion and the fourth wire portion;

connecting the first wire portion of the steering wire to a steerable tip part of the endoscope;

positioning the second wire portion adjacent the third wire portion;

applying an adhesive that is hardenable or settable on at least one surface of at least one of the second wire portion and the third wire portion;

positioning a crimp shell in proximity of the second wire portion and the third wire portion with the crimp shell attaching and at least partly enclosing the adhesive, the second wire portion, and the third wire portion; and crimping the crimp shell to form a crimp securing the second wire portion to the third wire portion, wherein a yield detachment force, measured after setting or hardening of the adhesive, required to detach the second wire portion and/or the third wire portion from the crimp exceeds about 40 N, the yield detachment force being applied by pulling the second wire portion and the third wire portion in opposite directions.

2. The method of claim 1, further comprising tensioning the steering wire before crimping the crimp shell.

3. The method of claim 2, the control element including an operating member, a rotation axis, and a lever extending from the rotation axis and connected to the operating member, whereby movement of the operating member causes the control element to rotate about the rotation axis, wherein positioning the second wire portion adjacent the third wire portion comprises forming a loop with the steering wire, the method further comprising coupling the loop to the control element prior to and to enable tensioning of the steering wire.

4. The method of claim 1, wherein positioning the crimp shell comprises aligning the crimp shell, the adhesive, and a crimp tool such that when crimping the crimp shell with the crimp tool a deformity in the crimp shell and the steering wire is formed, the deformity comprising at least a portion of the adhesive.

5. The method of claim 1, wherein the yield detachment force of the crimp measured after setting or hardening of the adhesive is between about 50-65 N.

6. The method of claim 1, wherein passing a steering wire through an insertion tube is performed after connecting the first wire portion of the steering wire.

7. The method of claim 1, further comprising allowing the adhesive to harden or set after crimping the crimp shell.

8. The method of claim 7, wherein the steering wire comprises at least two strands, and wherein applying an adhesive on at least one of the second wire portion and the third wire portion includes allowing the adhesive to distribute between at least two strands of the second wire portion and/or the third wire portion before the adhesive hardens or sets.

9. The method of claim 1, wherein applying an adhesive on at least one of the second wire portion and the third wire portion comprises applying the adhesive as a liquid adhesive on at least one of the second wire portion and the third wire portion.

10. The method of claim 1, wherein applying an adhesive on at least one of the second wire portion and the third wire portion comprises distributing the adhesive on a length of at least one of the second wire portion and the third wire portion, the length being equal to or above a diameter or a cross-sectional width of the steering wire.

11. The method of claim 1, wherein applying an adhesive on at least one of the second wire portion and the third wire portion comprises applying the adhesive at least partly between the second wire portion and the third wire portion.

12. The method of claim 1, further comprising gripping a crimping tool including a first part having a protrusion and a second part having a depression corresponding to the protrusion of the first part, wherein crimping the crimp shell comprises applying a crimping force to the crimping tool to cause the protrusion and the depression to deform the crimp shell and form a crimp.

13. The method of claim 1, wherein the crimp shell comprises a steel ferrule having a cylindrical portion and a flared portion extending from the cylindrical portion.

14. An endoscope comprising:
   an operating handle;
   an insertion tube with a proximal end and a distal end, and with a steerable tip part located at the distal end;
   a control element movable in relation to the operating handle;
   a steering wire comprising a stranded plastic polymer including first, second, and third wire portions, the first wire portion being connected to the steerable tip part, and the second wire portion being located between the first and third wire portions;
   an adhesive that is hardenable or settable and is located on at least one surface of at least one of the second and third wire portions; and
   a crimp shell comprising a crimp formed by application of a crimping force to deform the crimp shell, the crimp attaching and at least partly enclosing the second wire portion, the third wire portion, and at least a portion of the adhesive,
   wherein a yield detachment force, measured after setting or hardening of the adhesive, required to detach the second wire portion and/or the third wire portion from the crimp exceeds about 40 N, the yield detachment force being applied by pulling the second wire portion and the third wire portion in opposite directions.

15. The endoscope of claim 14, wherein the yield detachment force of the crimp measured after setting or hardening of the adhesive is between about 50-65 N.

16. The endoscope of claim 14, wherein the adhesive adheres the crimp shell to at least one of the second and third wire portions, or the second and third wire portions to each other, or at least two strands of one of the second and third wire portions to each other.

17. The endoscope of claim 14, wherein the adhesive is a single component, anaerobic, cyanoacrylate, heat hardenable, moisture hardenable, radiation hardenable and/or silicone adhesive.

18. The endoscope of claim 16, wherein portions of the adhesive are located and distributed between strands of the steering wire inside the crimp.

* * * * *